US011872582B2

(12) United States Patent
Barthelmes et al.

(10) Patent No.: US 11,872,582 B2
(45) Date of Patent: Jan. 16, 2024

(54) ELECTROSTATIC ATOMIZER FOR LIQUIDS AND METHOD FOR OPERATING AN ELECTROSTATIC ATOMIZER

(71) Applicant: J. Wagner GmbH, Markdorf (DE)

(72) Inventors: Jan Barthelmes, Salem (DE); Alfred Göhring, Salem (DE); Thomas Jeltsch, Friedrichshafen (DE); Holger Stohl, Markdorf (DE)

(73) Assignee: J. Wagner GmbH, Markdorf (DE)

( * ) Notice: Subject to any disclaimer, the term of this patent is extended or adjusted under 35 U.S.C. 154(b) by 433 days.

(21) Appl. No.: 16/657,117

(22) Filed: Oct. 18, 2019

(65) Prior Publication Data

US 2020/0114376 A1 Apr. 16, 2020

Related U.S. Application Data

(63) Continuation of application No. PCT/EP2018/060117, filed on Apr. 19, 2018.

(30) Foreign Application Priority Data

Apr. 21, 2017 (DE) ..................... 10 2017 108 610.2

(51) Int. Cl.
*B05B 5/025* (2006.01)
*A45D 34/04* (2006.01)
(Continued)

(52) U.S. Cl.
CPC ............ *B05B 5/0255* (2013.01); *A45D 34/04* (2013.01); *B05B 5/001* (2013.01); *B05B 5/053* (2013.01);
(Continued)

(58) Field of Classification Search
CPC ............ B05B 1/14; B05B 5/001; B05B 5/053; B05B 9/0423; B05B 15/16; B05B 15/68;
(Continued)

(56) References Cited

U.S. PATENT DOCUMENTS 4,467,961 A    8/1984   Coffee et al.
6,021,965 A *   2/2000   Hartle .................... B05B 5/001
                                                                   138/120

(Continued)

FOREIGN PATENT DOCUMENTS

CN    202802424 U    3/2013
CN    103846171 A    6/2014
(Continued)

OTHER PUBLICATIONS

English translation of International Preliminary Report on Patentability (Chapter 1) (Application No. PCT/EP2018/060117) dated Oct. 31, 2019, 33 pages.

(Continued)

*Primary Examiner* — Cody J Lieuwen
(74) *Attorney, Agent, or Firm* — BURR PATENT LAW, PLLC

(57) ABSTRACT

The invention relates to an electrostatic atomizer for liquids, in particular, cosmetics, the atomizer comprising a housing, an electrical energy source, an activation mechanism, control electronics, a high-voltage source, a liquid tank, a delivery device and atomizer nozzles. The delivery device is arranged here between the liquid tank and the atomizer nozzles, the delivery device being connected to the liquid tank by a first line and the delivery device being connected to the atomizer nozzles by a second line, so that the delivery device sucks liquid out of the liquid tank and delivers it to the atomizer nozzles.

23 Claims, 5 Drawing Sheets

(51) Int. Cl.
*B05B 5/00* (2006.01)
*B05B 5/053* (2006.01)
*B05B 5/16* (2006.01)
*B05B 1/14* (2006.01)

(52) U.S. Cl.
CPC ...... *B05B 5/1691* (2013.01); *A45D 2200/057* (2013.01); *B05B 1/14* (2013.01)

(58) Field of Classification Search
CPC ..... B05B 15/70; B05B 5/0537; B05B 5/0538; B05B 5/1691; A45D 34/02; A45D 34/04; A45D 2200/054; A45D 2200/056; A45D 2200/057; A45D 2034/005; A61M 35/003; A61M 35/25; A61M 35/30
See application file for complete search history.

(56) References Cited

U.S. PATENT DOCUMENTS

| | | | |
|---|---|---|---|
| 2001/0038047 A1* | 11/2001 | Wilson | B05B 5/1691 239/690 |
| 2003/0029447 A1* | 2/2003 | Vito | A61M 15/0088 128/200.23 |
| 2003/0033726 A1 | 2/2003 | Saida | |
| 2004/0079360 A1* | 4/2004 | Coffee | A61M 15/008 128/200.14 |
| 2005/0212879 A1 | 9/2005 | Chiao et al. | |
| 2008/0190359 A1 | 8/2008 | Mauchle et al. | |
| 2009/0008481 A1 | 1/2009 | Smith et al. | |
| 2009/0200392 A1* | 8/2009 | Duru | B05B 17/0623 239/13 |
| 2010/0051649 A1 | 3/2010 | Ki | |
| 2010/0116897 A1 | 5/2010 | Lind et al. | |
| 2011/0076411 A1 | 3/2011 | Nussbaum | |
| 2012/0125950 A1 | 5/2012 | Bouix et al. | |
| 2012/0248149 A1* | 10/2012 | Pelfrey | A47K 5/1215 222/214 |
| 2016/0192760 A1* | 7/2016 | Nishiura | B05B 7/2416 239/337 |

FOREIGN PATENT DOCUMENTS

| | | | | |
|---|---|---|---|---|
| EP | 1 388 371 A2 | 2/2004 | | |
| EP | 1388371 A2 * | 2/2004 | ......... | A61L 26/0076 |
| JP | 2000-516130 A | 12/2000 | | |
| JP | 2003-059622 A | 2/2003 | | |
| JP | 2008-246291 A | 10/2008 | | |

OTHER PUBLICATIONS

International Search Report and Written Opinion (Application No. PCT/EP2018/060117) dated Sep. 5, 2018.
Chinese Office Action (Application No. 2018800416013) dated Jan. 5, 2021 (English translation only).
Japanese Office Action (Application No. 2019-557480) dated Jan. 11, 2022 (with English translation).
Japanese Office Action (with English translation) dated Aug. 16, 2022 (Application No. 2019-557480).

* cited by examiner

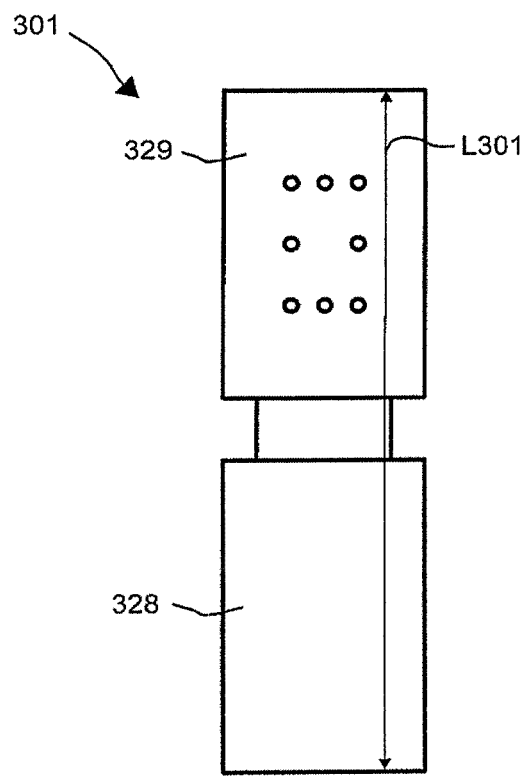 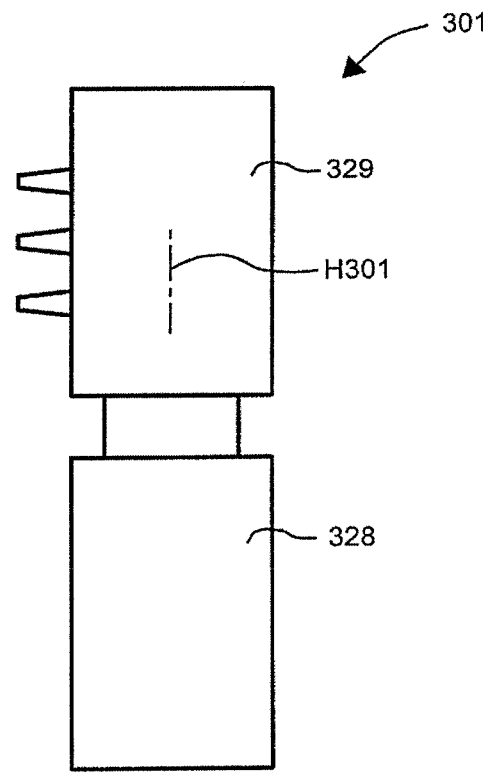
Fig. 5a    Fig. 5b
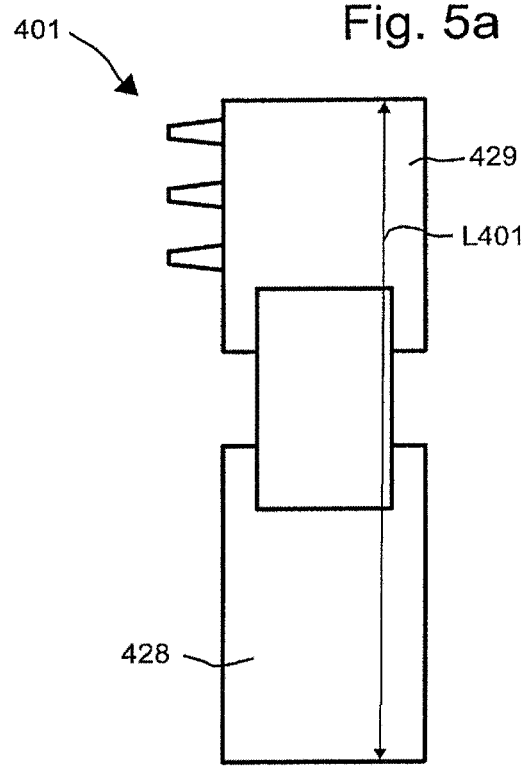 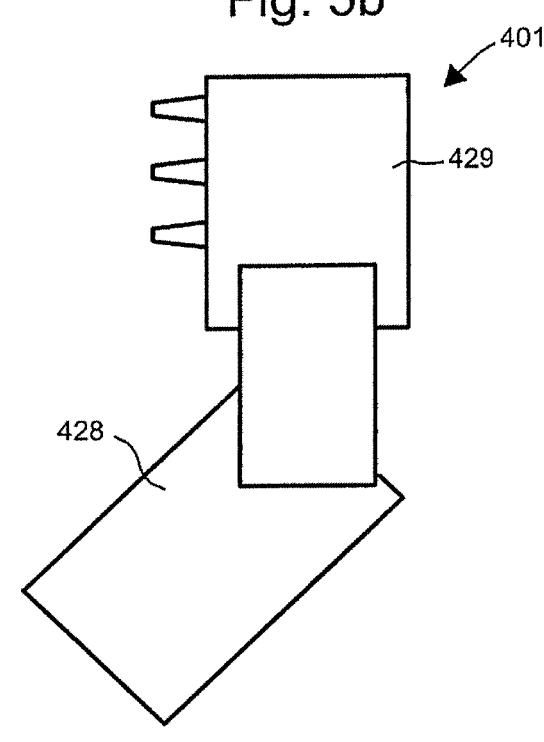
Fig. 6a    Fig. 6b

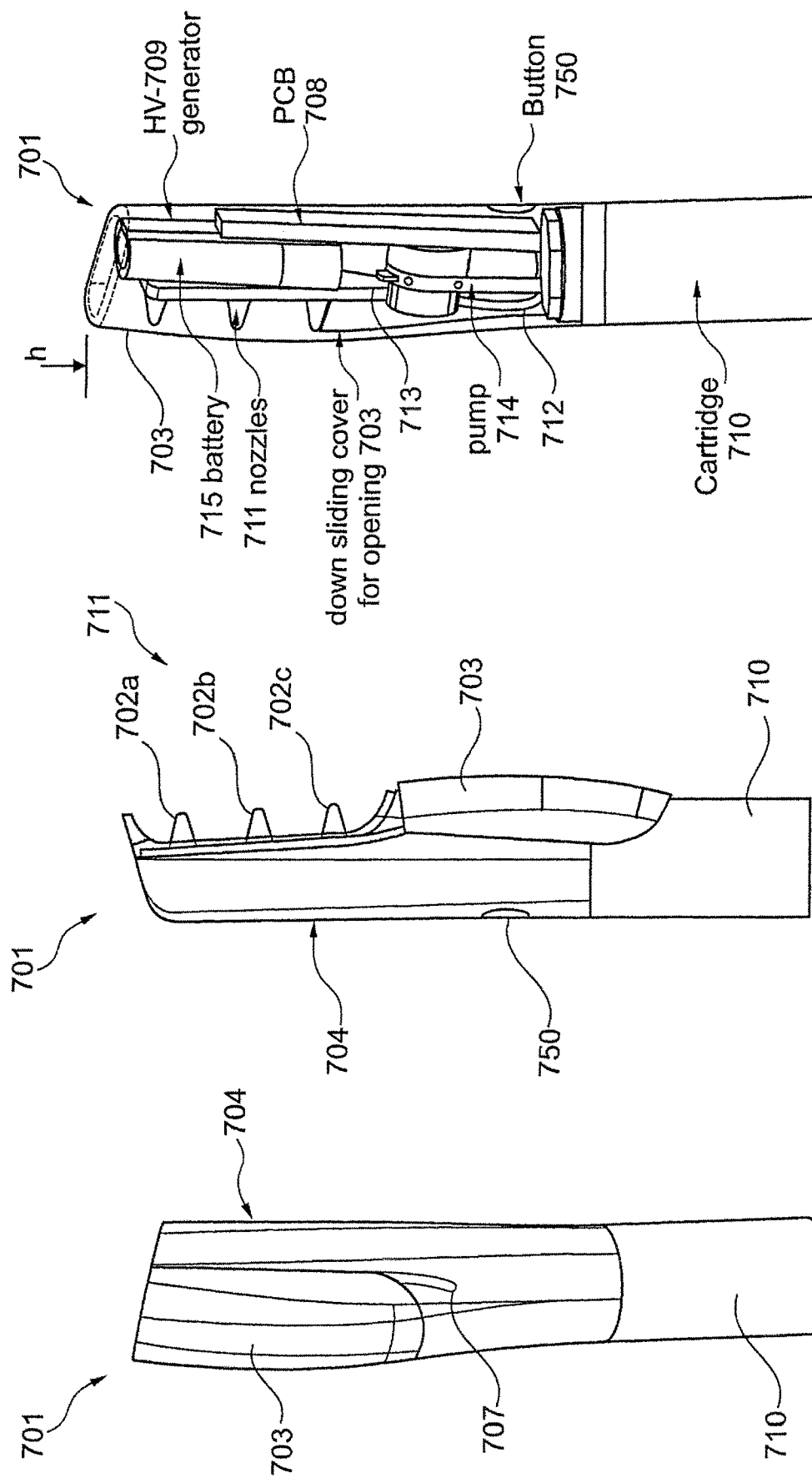

ELECTROSTATIC ATOMIZER FOR LIQUIDS AND METHOD FOR OPERATING AN ELECTROSTATIC ATOMIZER

CROSS REFERENCE TO RELATED APPLICATIONS

This application is a continuation of International Application No. PCT/EP2018/060117 filed Apr. 19, 2018, which designated the United States, and claims the benefit under 35 USC § 119(a)-(d) of German Application No. 10 2017 108 610.2 filed Apr. 21, 2017, the entireties of which are incorporated herein by reference.

FIELD OF THE INVENTION

The present invention relates to an electrostatic atomizer for liquids and a method for operating an atomizer.

BACKGROUND OF THE INVENTION

In the context of the present invention, electrostatic atomization comprises all atomization processes that atomize liquids with effects under the influence of a high voltage. In particular, electrohydrodynamic effects and electrokinetic effects are also covered by the concept of this type of atomization. In the context of the present invention, an electrostatic atomization may also be understood as meaning an electrohydrodynamic atomization.

US 2010/0116897 A1 discloses an electrostatic atomizer for liquids which comprises a housing, an electrical energy source, an activation mechanism, control electronics, a high-voltage source, a liquid tank, a delivery device and atomizer nozzles. A delivery of the liquid is performed by a piston guided on a spindle in the liquid tank.

SUMMARY OF THE INVENTION

The present invention is based on the object of proposing an electrostatic atomizer for liquids and a method for operating an atomizer with which and by which reliable emptying of the liquid tank and reliable supplying of the atomizer nozzles are ensured, while at the same time the liquid tank can be produced at low cost.

In the case of the electrostatic or electrohydrodynamic atomizer according to the present invention for liquids, in particular cosmetics, the delivery device is arranged between the liquid tank and the atomizer nozzles, the delivery device being connected to the liquid tank by a first line and the delivery device being connected to the atomizer nozzles by a second line, so that the delivery device sucks liquid out of the liquid tank and delivers it to the atomizer nozzles. Such an arrangement of the delivery device between the liquid tank and the atomizer nozzles or in a liquid conduit makes it possible to design the liquid tank as a simply constructed, passive component. The sucking design of the delivery device means that the liquid tank itself does not require any pressure-generating component parts. In this way, the liquid can also be passed on to the atomizer nozzles without any load being imposed on the liquid tank.

The first and second lines may in this case preferably be formed in one piece, in particular, provided as an extruded plastic hose that can be produced at low cost. Such hoses are known from the area of hose pumps in the form of peristaltic pumps. According to the present invention, however, it is preferably provided that, for each atomizer nozzle, a separate hose leads from the liquid tank to the atomizer nozzle, and, in particular, each hose comprises a delivery device, in particular, a hose pump, or the hoses conduct the liquid to the respective atomizer nozzles as a hose assembly (for example, similar to a ribbon cable) with a delivery device, in particular, a multi-channel hose pump.

In the context of the present invention, a grid may also be understood as meaning an arrangement of a number of columns arranged next to one another and rows arranged below one another.

Alternatively, in the context of the present invention, a grid may also comprise the corner points of a triangle, as is the case, for example, with a crystal lattice of the diamond structure.

In the context of the present invention, a liquid should be understood as meaning any kind of liquid. In the context of the present invention, it is provided, in particular, that the liquid is a cosmetic, a sunscreen or an insect repellent. Use of a skin coloring agent for tanning or lightening the skin is also conceivable.

The liquid may, however, also be a liquid paint or lacquer or the like.

BRIEF DESCRIPTION OF THE DRAWINGS

Further details of the present invention are described in the drawing on the basis of schematically represented exemplary embodiments.

FIG. 5a shows a schematic side view of a third variant of an embodiment of an atomizer;

FIG. 5b shows the atomizer shown in FIG. 5a, with a head portion turned by 90° with respect to the grip portion;

FIG. 6a shows a schematic side view of a fourth variant of an embodiment of an atomizer;

FIG. 6b shows the atomizer shown in FIG. 6a, with a grip portion tilted by 45° with respect to the head portion;

FIG. 7a shows an alternative embodiment comprising three atomizer nozzles with a slide in the closed state;

FIG. 7b shows the alternative embodiment comprising three atomizer nozzles with a slide in the open state; and FIG. 7c shows the alternative embodiment, with the subassemblies that are in the interior of the housing being shown.

DETAILED DESCRIPTION OF THE INVENTION

Figure 1:
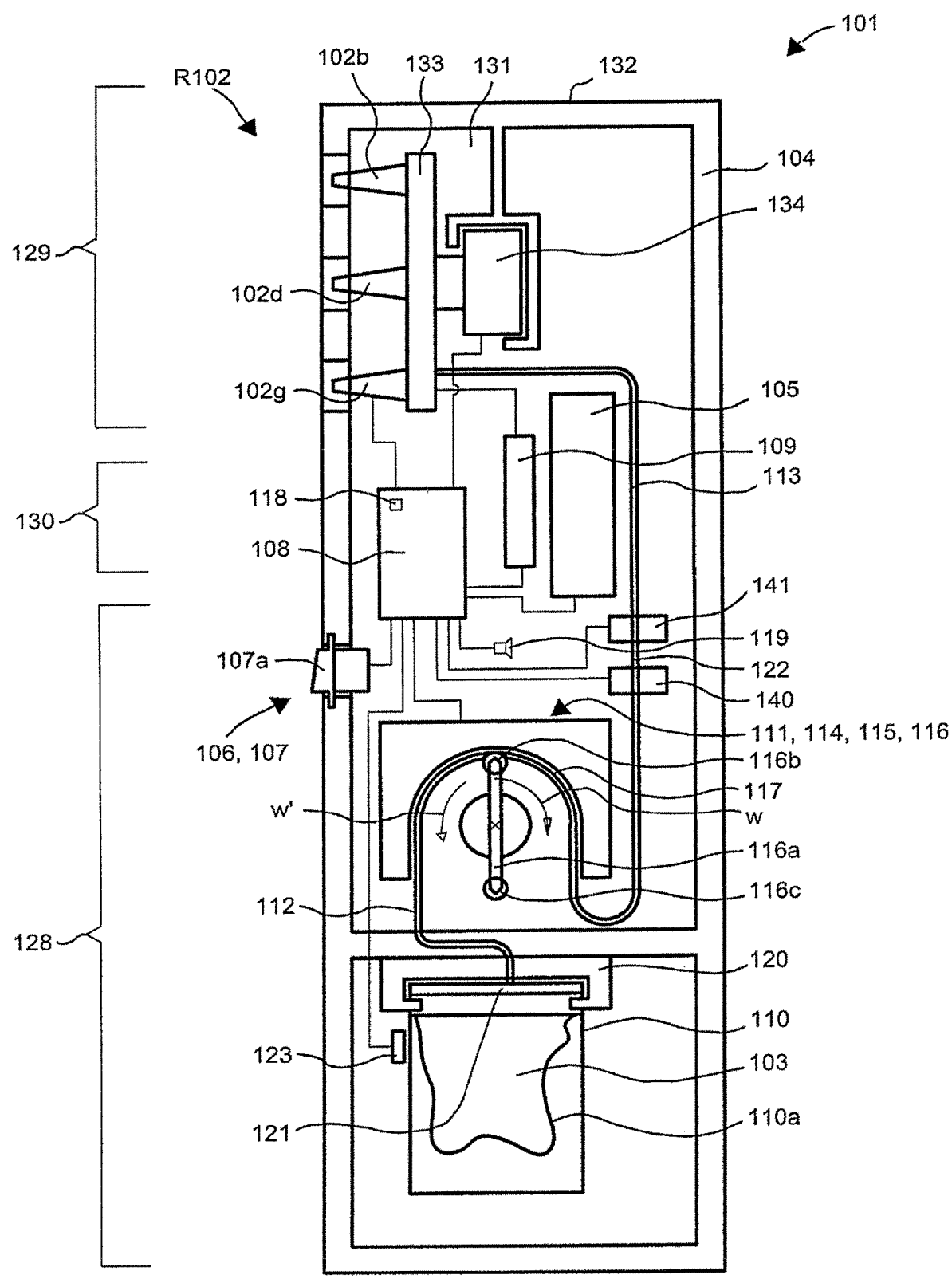
FIG. 1 shows a sectional view through a schematic representation of a first variant of an embodiment of an atomizer, the atomizer nozzles being in an inactive position.
Figure 2:
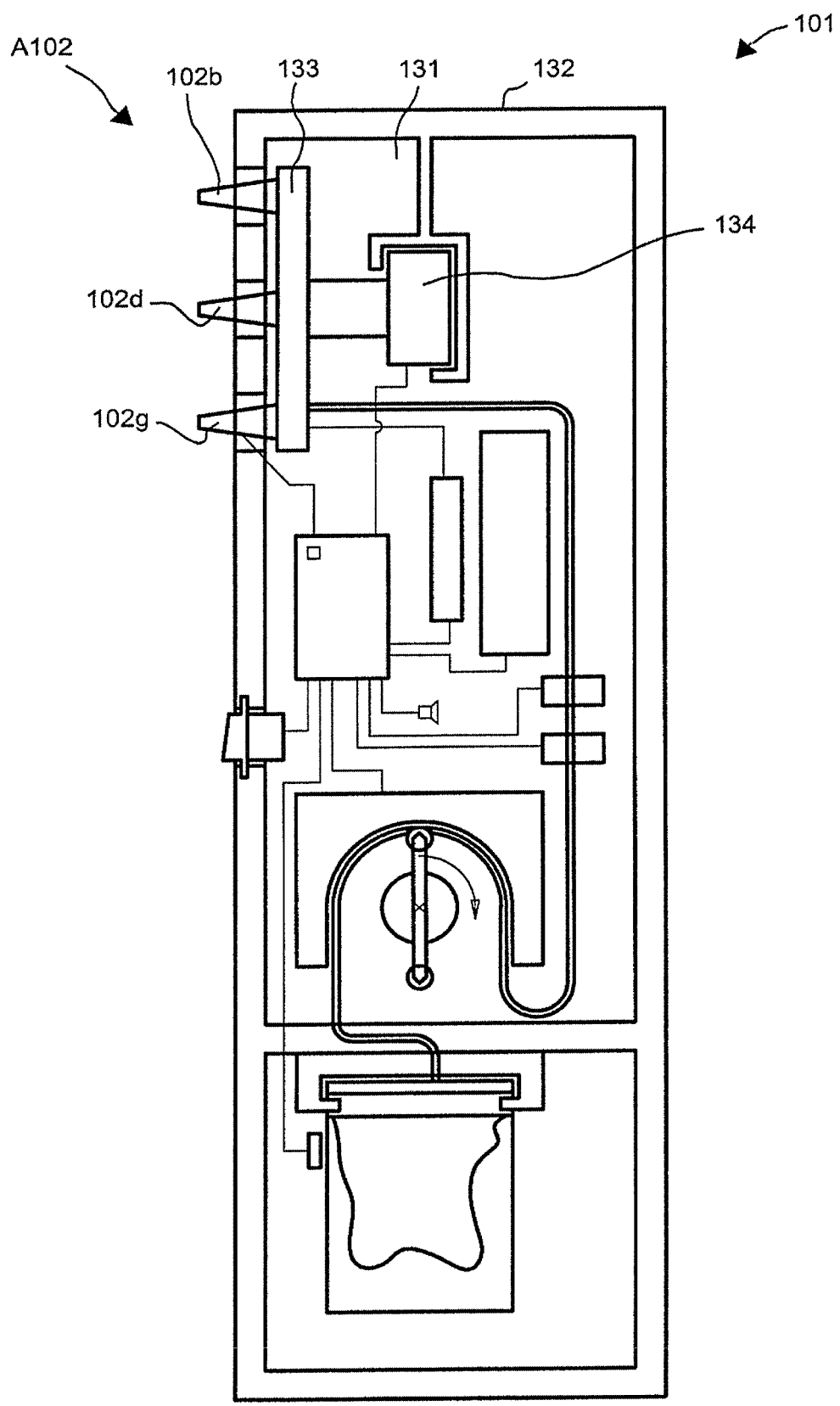
FIG. 2 shows a sectional view through the representation of FIG. 1, the atomizer nozzles being in an active position.
Figure 3:
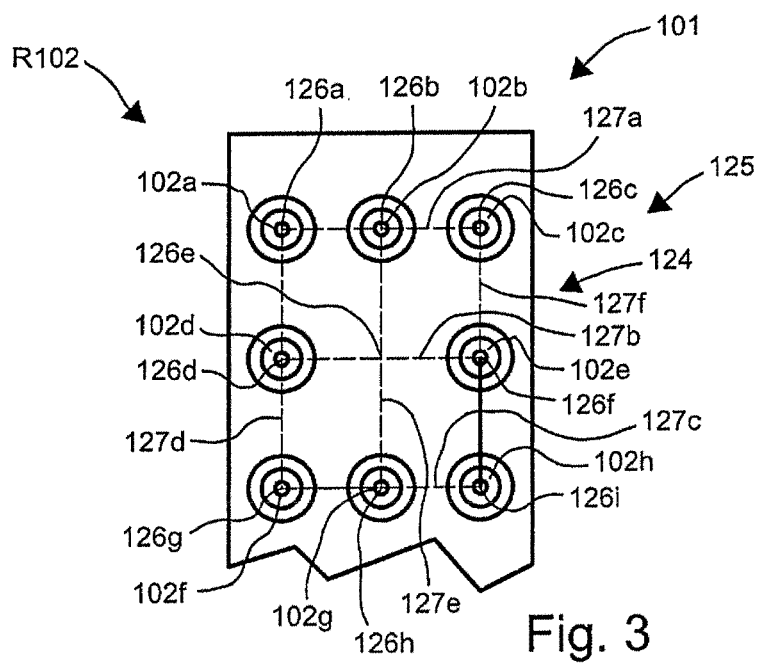
FIG. 3 shows a side view of FIG. 1 in the region of the atomizer nozzles.

In FIG. 1, a sectional view through a schematic representation of a first variant of an embodiment of an atomizer 101 is shown, with atomizer nozzles 102a to 102h being in an inactive position R102. In FIG. 2, the atomizer 101 shown in FIG. 1, comprising atomizer nozzles 102a to 102h that are in an active position A102, is shown. FIG. 3 finally shows a view of the atomizer 101 represented in FIG. 1 as a detail in the region of its atomizer nozzles 102a to 102h.

The electrostatic atomizer 101 is intended for electrostatic atomization of liquids 103. Liquids are understood here as meaning, in particular, cosmetics in a broader sense, but also, for example, paints and lacquers. The atomizer 101 comprises a housing 104, an electrical energy source 105, an activation mechanism 106, which is designed as an electrical button 107, control electronics 108, a high-voltage source 109, a liquid tank 110, a delivery device 111 and the mentioned atomizer nozzles 102a to 102h. The delivery device 111 is arranged between the liquid tank 110 and the atomizer nozzles 102a to 102h. The delivery device 111 is connected here to the liquid tank 110 by a first line 112 and the delivery device 111 is connected here to the atomizer nozzles 102a to 102h by a second line 113, so that during spraying operation the delivery device 111 sucks liquid 103 out of the liquid tank 110 and delivers it to the atomizer nozzles 102a to 102h. The line 112 and 113 is represented in the present case as a one-piece continuous hose. For reasons of overall clarity, only one hose to the nozzle array of the atomizer nozzles is represented. The atomizer nozzles may however be supplied by a number of hoses, in particular, one hose for each atomizer nozzle or else one hose for a group of a number of atomizer nozzles. In the case of the use of a number of hoses, a multiple hose pump should also be provided, one which can pump in parallel through a number of hoses, arranged in the manner of a flat band (similar to a ribbon cable), for example, by a broadening rotor.

The delivery device 111 is formed as a pump 114, specifically a positive displacement pump, in particular a peristaltic pump in the style of a suction pump 115. The suction pump 115 is formed as a hose pump 116 and is designed such that, during pumping operation, a delivery hose 117 arranged between the first line 112 and the second line 113 is alternately deformed in a rolling manner by rollers 116*b*, 116*c* arranged on a rotor 116*a*, and thereby completely pinched, as is shown in FIG. 1 in the region of the roller 116*b*.

The atomizer 101 comprises a switching device 118, by means of which a direction of rotation of the rotor 116*a* of the hose pump 116 can be switched over in such a way that the hose pump alternates between a delivery mode, in which the rotor 116*a* turns in a direction of rotation w, and a return mode, in which the rotor 116*a* turns in an opposite direction of rotation w'. A short return mode makes it possible to avoid an undesired escape of liquid 103 after spraying. It is intended here to avoid a return of the liquid 103 into the liquid tank 110. This is achieved by the first line 112, which like the delivery hose 117 is formed as elastically expandable, being slightly expanded by the return to increase the size of its inner volume, and the liquid tank 110 remaining closed by a nonreturn valve that is not represented. In order to ensure a great storage volume of the first line for a return, it is envisaged to make the first line at least 1.5 times and, in particular, twice as long as is required for connecting the liquid tank to the delivery device. Alternatively, it is also envisaged to conduct small amounts of liquid via a diverter or a corresponding valve into a disposal tank during the return mode. This makes it possible to empty the second line 113 largely completely.

The delivery device 101 and the high-voltage source 109 can be activated by way of the activation mechanism 106, which is formed by the electrical button 107. The button may however in this case also be formed as an electronic button, in particular, as a capacitive sensor, as a dry-reed contact or else as a Hall sensor. In the case of the activation mechanism, an actuating element 107*a* of the button 107 is electrically conductive and is formed as an opposite pole in relation to the atomizer nozzles 102*a* to 102*b*. Since the button 107 has to be pressed for a sustained time for spraying, in this way good connection of the user to the reference potential of the spray device 101 is ensured.

The atomizer 101 comprises an acoustic signal transmitter 119, which is connected to the control electronics 108. As a result, the user can be informed acoustically of a correct or incorrect use of the atomizer 101, and the handling of the atomizer 101 can in this way be trained and optimized. Also provided in addition or besides is a vibrating signal transmitter, this always being active at a specific frequency when the atomizer is spraying. By vibrating at a different frequency, further information can be conveyed to the user.

The atomizer 101 comprises a connection mechanism 120, the liquid tank 110 being connected to the connection mechanism 120 releasably and by way of a self-closing valve 121. As a result, a coupling and decoupling of the liquid tank 110 is possible by easy manual movements, and as a result undesired running out from the liquid tank 110 is also effectively prevented.

The liquid tank 110 is formed as a self-collapsing tank, and for this purpose comprises a film bag 110*a*. Such liquid tanks can be produced at low cost. Furthermore, with appropriate use of transparent components and/or appropriate positioning of openings, the filling level of such liquid tanks can be easily established by visual inspection.

The first line 112, the second line 113 and the delivery hose 117 are formed as one part, and are formed by a connecting hose 122. As a result, the number of connecting points is reduced, so that the risk of deposits forming is reduced.

Between the liquid tank 110 and the control electronics 108 is a detector 123 for identifying the liquid tank 110, the detector 123 being formed to detect information printed on the liquid tank or stored on the liquid tank and pass corresponding information on to the control electronics. As a result, the control electronics 108 are able to adapt various parameters, such as the level of the high voltage, the output of the pump, etc., to the liquid 103 to be sprayed. The identifying means may be formed in particular as RFID markings, which can be read by the control electronics 108 in the atomizer. It is particularly preferred that the control electronics 108 can also write the markings, in particular, the RFID markings. As a result, for example, a date on which a liquid tank was used for the first time or what amount has already been taken can be noted.

The atomizer 101 comprises 8 atomizer nozzles 102*a* to 102*h*, which are arranged in the manner of a ring (see FIG. 3). As a result, solid areas of several square centimeters can be sprayed, so that it is ensured that spraying makes rapid progress.

The atomizer nozzles 102*a* to 102*h* form a nozzle array 124 (see FIG. 3), the nozzle array 124 being formed as a grid 125 with grid lines 127*a* to 127*f* crossing at grid points 126*a* to 126*i*, it being provided, in particular, that the atomizer nozzles 102*a* to 102*h* form grid points of parallel grid lines. Such a regular geometrical arrangement allows a more uniform application of the liquid to be achieved.

It is also evident from FIGS. 1 and 2 that the housing 101 comprises a grip portion 128, a head portion 129 and a middle portion 130 arranged between the grip portion 128 and the head portion 129, the atomizer nozzles 102*a* to 102*h* being arranged in the head portion 129, the delivery device 111 being arranged between the liquid tank 110 and the atomizer nozzles 102*a* to 102*h*.

As is evident from FIG. 1, it is also provided that the atomizer 101 comprises a heating device 140 and a cooling device 141, it being possible as a result for the liquid 103 to be heated or cooled to achieve a prescribed temperature and/or viscosity before leaving the atomizer nozzles 102a to 102h.

Alternatively, it is also envisaged to arrange the liquid tank between the delivery device and the atomizer nozzles.

Figures 4A, 4B:
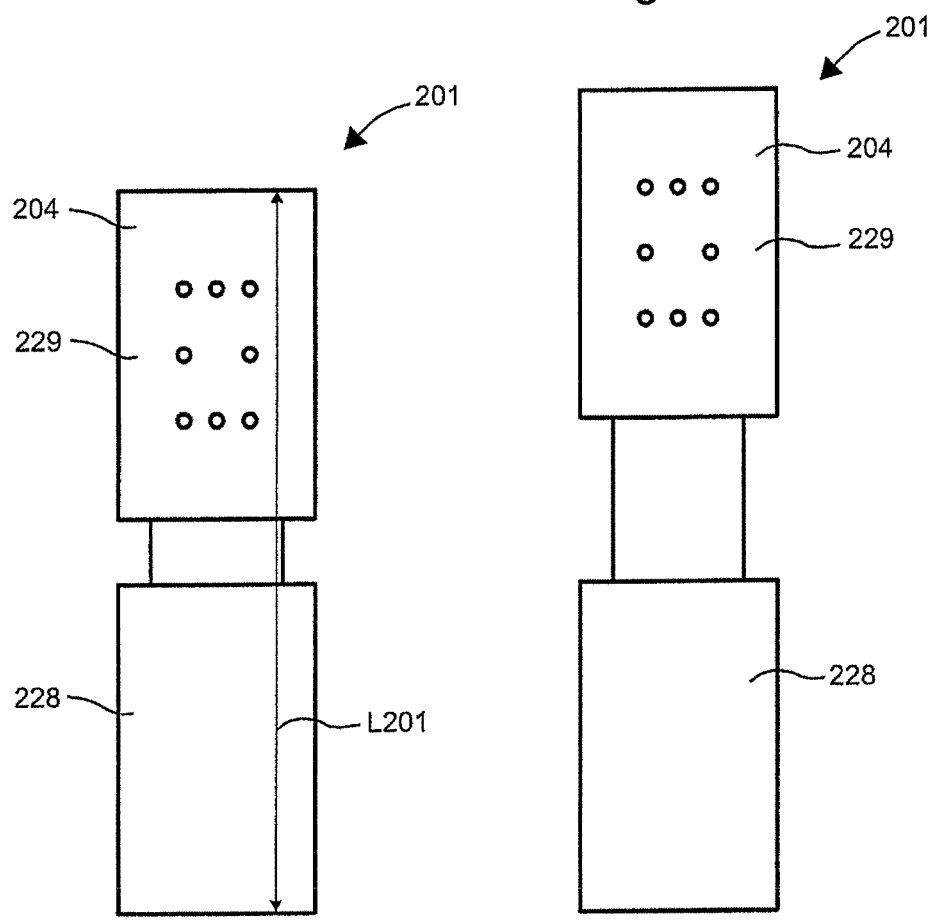
FIG. 4a shows a schematic side view of a second variant of an embodiment of an atomizer.
FIG. 4b shows the atomizer shown in FIG. 4a in a telescoped position.

FIGS. 4a and 4b show a second variant of an embodiment of an atomizer. In the case of the atomizer 201, a housing 204 is designed as telescopic, so that a distance between a head portion 229 and a grip portion 228 is variable (compare FIGS. 4a and 4b). As a result, spraying of the feet for example is made easier for a user.

FIGS. 5a and 5b show a third variant of an embodiment of an atomizer. In the case of the atomizer 301, a head portion 329 and a grip portion 328 can be turned with respect to one another. In FIG. 5a, the atomizer 301 is shown unturned and in FIG. 5b the head portion 329 is turned by 90° to the right about a vertical axis H301 with respect to the grip portion 328, on which an activation mechanism that is not represented is also arranged. Such a turning capability makes it easier for example to spray the shoulders.

FIGS. 6a and 6b show a fourth variant of an embodiment of an atomizer. The atomizer 401 has a grip portion 428, which can be tilted away with respect to a head portion 429 because the atomizer 401 comprises an articulated joint. As a result, for example spraying the soles of the feet or the back is made easier.

It goes without saying that it is also envisaged to combine the three forms of construction shown in FIGS. 4a to 6a, and thus their advantages, so that an atomizer that is optimally suited for the actual use is formed.

In the case of the atomizers 201, 301 and 401, it is envisaged to form them with a length L201 or L301 or L401, respectively, of approximately 10 cm to 25 cm, in the case of the telescopic atomizer 201 the length L204 indicating the length that it has in the pushed-together state (see FIG. 4a).

According to a variant of an embodiment that is not represented, it is also provided that the atomizer comprises in addition to the first liquid tank a second liquid tank, that the atomizer comprises in addition to the first delivery device a second delivery device and that arranged between the delivery devices and the atomizer nozzles is a mixing device. In this way, different liquids can be mixed. By making the delivery devices operate with different speeds of the rotors, the two liquids can also be mixed with a composition that differs in terms of quantities, so that, for example, the proportion of care substances can be increased or reduced.

A further variant of an embodiment that is not represented provides that the atomizer comprises a heating device and/or a cooling device, the liquid being heatable or coolable to achieve a prescribed temperature and/or viscosity before leaving the at least one atomizer nozzle. As a result, largely comparable spraying results can be achieved under different ambient conditions.

It is also envisaged to operate the atomizer in such a way that the delivery device is operated for delivering the liquid both in the feed direction, that is to say for transporting liquid from the liquid tank to the atomizer nozzles, and in the return direction, that is to say for transporting liquid from the atomizer nozzle in the direction of the liquid tank. Such a two-directional operation of the delivery device means that it has the associated additional benefit that an outflow of liquid after spraying can be reliably avoided.

In the case of the atomizer 101 shown in FIGS. 1 to 3, as already mentioned, switching over between an inactive position R102 and an active position A102 is possible. Here, the atomizer nozzles 102a to 102h in the inactive position R102 (see FIG. 1) are positioned in an interior space 131 of the housing 104 and in the active position A102 protrude at least partly beyond an outer side 132 of the housing 104 (see FIG. 2). For this purpose, the housing 104 and the atomizer nozzles 102a to 102h are movable in relation to one another, the atomizer nozzles 102a to 102h being arranged on a baseplate 133, and are able to be moved together with the latter in relation to the housing 104 by a lifting cylinder 134. Such a moving capability means that the atomizer nozzles 102a to 102h are protected from damage when the atomizer 101 is not in use. Furthermore, as a result, undesired catching of the atomizer 101, for example, when it is removed from a purse, is also reliably avoided.

Alternatively or besides, it is also envisaged to cover the atomizer nozzles by slides, flaps, lids and comparable covering means, or to allow them to project beyond an outer side of the housing. In particular, there is the possibility of providing these slides, flaps or lids with switches, in order, for example, to activate an operational readiness when the slide is open or a switching off of the unit when the slide is closed.

FIGS. 7a to c show in this respect a further variant of an embodiment 701 of the atomizer according to the invention. FIG. 7a shows in this case the atomizer 701 with a housing 704. Arranged at the lower end of the housing 704 is a liquid tank 710, which in the present case is formed as a tank with a passive follow-up piston (not represented). At the upper end, the housing 704 has a slide 703, which in FIG. 7a is shown closed. By displacing the slide 703 along a guide 707 in the direction of the lower end of the housing 704, the slide 703 is brought into the position represented in FIG. 7b. This displacing of the slide 703 has the effect that a nozzle array 711 with three atomizer nozzles 702a, 702b and 702c is exposed. The slide has in this case switching means, which only establish an operational readiness of the atomizer 701, and expose the necessary components on the control electronics 708, when the slide 703 is open, that is to say in the position corresponding to FIG. 7b.

The nozzle array 711 comprises in the present case three atomizer nozzles 702a, 702b, 702c, which in the version represented are produced from silicone. According to the present invention, other materials, in particular, also hard plastics such as, for example, PE or PP, that are suitable for the electrostatic interaction for the atomization are also conceivable. The high voltage from the high-voltage source 709 that is used for the atomization allows a good atomizing result to be achieved, in particular, in the case of silicone nozzles.

In FIG. 7b, an electrical button 750 is provided on the side opposite from the slide 703. This button serves for activating the spraying operation. Apart from a simple electrical button, an electronic switch may also be provided, for example, by a capacitive or similar switch triggering. A contact face on the button serves for the electrical contacting of the user, to avoid charges due to the electrostatic atomization.

FIG. 7*c* shows the schematic arrangement of the components of the embodiment represented of the atomizer 701. Arranged above the liquid tank 710 is a hose pump 714. The atomizer nozzles 702*a*, 702*b* and 702*c* are connected by way of a hose assembly 713 comprising three hoses, each atomizer nozzle being connected to a hose of its own, via the hose pump 714 in the configuration of a multi-channel pump to the liquid tank by way of a hose assembly 712. The hose assemblies are in this case formed as hoses that are lying next to one another and are extruded in one piece, comparable to the arrangement of a ribbon cable.

Arranged behind the hose pump 714 are control electronics 708. Also represented in FIG. 7c, on the rear side of the housing 704, is the button 750 for operating the atomizer and contacting the operator. Arranged above the hose pump 714 is a battery 715 as an energy source. The battery 715 is in this case accommodated in a space-saving manner behind the nozzle array 711, in the present case in FIG. 7c the slide 703 having been pushed up and the nozzle array 711 covered. The overall arrangement has a height h of about 27 cm, and is consequently handy to operate and at the same time capable of making it possible to reach difficult places, for example on an operator's back.

It is also envisaged to combine the features described in relation to the individual variants of an embodiment with one another in order to bring together the advantages of individual variants of the atomizer in one atomizer.

LIST OF DESIGNATIONS

101 Atomizer (first variant)
102a-102h Atomizer nozzle
103 Liquids
104 Housing
105 Energy source
106 Activation mechanism (switch or button)
107 Electrical button
107a Actuating element of 107
108 Control electronics
109 High-voltage source
110 Liquid tank
110a Film bag
111 Delivery device
112 First line
113 Second line
114 Pump
115 Suction pump
116 Hose pump
117 Delivery hose
116a Rotor
116b, 116c Roller
117 Delivery hose
118 Switching device
119 Signal transmitter
120 Connection mechanism
121 Valve
122 Connecting hose
123 Detector for identifying the liquid tank
124 Nozzle array
125 Grid
126a-126i Grid point
127a-127f Grid line
128 Grip portion
129 Head portion
130 Middle portion
131 Interior space
132 Outer side
133 Baseplate
134 Lifting cylinder
140 Heating device
141 Cooling device
A102 Active position
R102 Inactive position
w, w' Direction of rotation
201 Atomizer
204 Housing
228 Grip portion
229 Head portion
L201 Length of 201
301 Atomizer
328 Grip portion
329 Head portion
H301 Vertical axis of 301
L301 Length of 301
401 Atomizer
428 Grip portion
429 Head portion
L401 Length of 401
701 Atomizer
702a-702c Atomizer nozzles
703 Slide
704 Housing
707 Guide
708 Control electronics
709 High-voltage source
710 Liquid tank
711 Nozzle array
712 Hose assembly
713 Hose assembly
714 Hose pump
715 Battery
750 Button
h Height of the unit

The invention claimed is:
1. An electrostatic liquid atomizer comprising:
a housing;
an electrical energy source;
an activation mechanism comprising an activation button;
control electronics;
a voltage source having a pair of opposite poles;
a liquid tank;
a delivery device comprising a multiple hose pump;
atomizer nozzles; and
a switch that changes a rotation direction of a rotor of the hose pump between a delivery mode and a return mode,
wherein the activation mechanism further comprises electrical contacts to open and/or close a circuit between the activation mechanism and the control electronics,
wherein the delivery device is arranged between the liquid tank and the atomizer nozzles,
wherein the delivery device is connected to the liquid tank by a first line,
wherein the delivery device is connected to the atomizer nozzles by a second line, so that the delivery device sucks liquid out of the liquid tank and delivers the liquid to the atomizer nozzles,
wherein during a pumping operation, the house pump performs in a rolling manner, thereby completely pinching a portion of a delivery hose arranged between the first line and the second line,
wherein the delivery device and the voltage source are activated by the activation mechanism, and wherein an actuating element of the activation button of the activating mechanism is constructed as a ground contact connected to one pole of the voltage source so as to have an opposite electrical polarity with respect to an electrical polarity of the atomizer nozzles,
wherein the first line, the second line and the delivery hose are integrally formed as an extruded plastic connecting hose, and
wherein the first line and the second line each comprise a number of hoses arranged in parallel and integrally formed continuously in one piece, and for each atomizer nozzle, a respective one of the number of hoses leads from the nozzle through the multiple hose pump of the delivery device to the liquid tank.

2. The atomizer as claimed in claim 1, wherein the multiple hose pump comprises a multi-channel peristaltic pump.

3. The atomizer as claimed in claim 1, wherein in the delivery mode, the multiple hose pump functions as a suction pump on the liquid tank side, and in the return mode, the hose pump functions as a pressure pump on the liquid tank side.

4. The atomizer as claimed in claim 1, wherein the atomizer further comprises a main switch, the main switch comprising a main switch slide, a main switch slide switch, a main switch button or a main switch sensor, and wherein the main switch enables an operating state of the atomizer.

5. The atomizer as claimed in claim 1, wherein the atomizer comprises an acoustic signal transmitter and/or an optical signal transmitter and/or a haptic connected to the control electronics.

6. The atomizer as claimed in claim 5, wherein the haptic comprises a vibrating signal transmitter.

7. The atomizer as claimed claim 1, wherein the atomizer comprises a connection mechanism, wherein the liquid tank is releasably connected to the connection mechanism via a self-opening and self-closing valve.

8. The atomizer as claimed in claim 1, wherein the liquid tank is a self-collapsing tank comprising a film bag or a container with a passively following piston.

9. The atomizer as claimed in claim 1, further comprising a detector for identifying the liquid tank that is located between the liquid tank and the control electronics and/or the housing for receiving the liquid tank, wherein the detector is formed as at least one of a mechanical coding, thereby forming an interlocking engagement, an electronic coding that transmits information about the liquid tank, and an electrical coding forming electrical line routes via contacts.

10. The atomizer as claimed in claim 9, wherein the electronic coding is an RFID coding.

11. The atomizer as claimed in claim 1, wherein the atomizer comprises at least 8 atomizer nozzles.

12. The atomizer as claimed in claim 11, wherein the atomizer comprises at least 20 atomizer nozzles.

13. The atomizer as claimed in claim 1, wherein the atomizer comprises at least two and at most 8 atomizer nozzles.

14. The atomizer as claimed in claim 1, the atomizer nozzles form a nozzle array defining a grid with grid lines crossing at grid points, and wherein the atomizer nozzles form grid points of parallel grid lines or corner points of a triangular grid structure.

15. The atomizer as claimed in claim 1, wherein the housing comprises a grip portion, a head portion and a middle portion arranged between the grip portion and the head portion, wherein the atomizer nozzles are arranged in the head portion, and/or wherein the housing of the atomizer has a length in a range of 10 cm to 30 cm.

16. The atomizer as claimed in claim 15, wherein the housing is telescopic, wherein a distance between the head portion and the grip portion is variable, and/or wherein the head portion and the grip portion can be turned with respect to one another, and/or wherein the head portion and the grip portion are variable with respect to an angle assumed in relation to one another by tilting.

17. The atomizer as claimed in claim 15, wherein the length of the housing is 27 cm.

18. The atomizer as claimed in claim 1, wherein the atomizer further comprises a second liquid tank, and/or wherein the atomizer further comprises a second delivery device, and/or wherein a mixing device is arranged between the delivery devices and the atomizer nozzles.

19. The atomizer as claimed in claim 1, wherein the atomizer comprises a heating device and/or a cooling device, and wherein the liquid is heatable or coolable to achieve a prescribed temperature and/or viscosity before leaving the atomizer nozzles.

20. A method for operating an atomizer as claimed in claim 1, wherein the delivery device is operated for delivering the liquid both in a feed direction from the liquid tank to the atomizer nozzles, and in a return direction from the atomizer nozzle in the direction of the liquid tank.

21. The atomizer as claimed in claim 1, wherein the hose pump comprises a suction pump for sucking liquid out of the liquid tank.

22. The atomizer as claimed in claim 1, wherein the first line, the second line and the delivery hose comprise a rubber hose.

23. An electrostatic atomizer for liquids, in particular cosmetics, comprising:
a housing;
an electrical energy source;
an activation mechanism comprising an activation button;
control electronics;
a voltage source having a pair of opposite poles;
a liquid tank;
a delivery device comprising a multiple hose pump; and
atomizer nozzles,
wherein the activation mechanism comprises electrical contacts to open and/or close a circuit between the activation mechanism and the control electronics,
wherein the control electronics and the voltage source are arranged in an interior space of the housing,
wherein the atomizers can be switched between an inactive position and an active position,
wherein the atomizer nozzles in the inactive position are positioned in the interior space of the housing,
wherein the atomizer nozzles in the active position project beyond an outer side of the housing,
wherein the housing and the atomizer nozzles are movable in relation to one another,
wherein during a pumping operation, the hose pump performs in a rolling manner, thereby completely pinching a portion of a delivery hose arranged between a first line connecting the delivery device to the liquid tank and a second line connecting the delivery device to the atomizer nozzles,
wherein the delivery device and the voltage source are activated by the activation mechanism, and wherein an actuating element of the activation button of the activating mechanism is constructed as a ground contact connected to one pole of the voltage source so as to have an opposite electrical polarity with respect to an electrical polarity of the atomizer nozzles,
wherein the first line, the second line and the delivery hose are integrally formed as an extruded plastic connecting hose, and
wherein the first line and the second line each comprise a number of hoses arranged in parallel and integrally formed continuously in one piece, and for each atomizer nozzle, a respective one of the number of hoses leads from the nozzle through the multiple hose pump of the delivery device to the liquid tank.

\* \* \* \* \*